United States Patent [19]

Levin

[11] Patent Number: 5,578,030
[45] Date of Patent: Nov. 26, 1996

[54] BIOPSY NEEDLE WITH CAUTERIZATION FEATURE

[76] Inventor: John M. Levin, 412 Fairview Rd., Narberth, Pa. 19072

[21] Appl. No.: 334,836

[22] Filed: Nov. 4, 1994

[51] Int. Cl.⁶ ........................................... A61B 10/00
[52] U.S. Cl. ................................. 606/39; 606/49
[58] Field of Search ........................ 606/27, 28, 29, 606/30, 31, 32, 33, 34, 35, 36, 37, 38, 39, 40, 41, 44, 45, 46, 48, 49, 50, 51, 52; 128/751

[56] References Cited

U.S. PATENT DOCUMENTS

| | | |
|---|---|---|
| 1,813,902 | 7/1931 | Bovie . |
| 2,275,167 | 3/1942 | Bierman . |
| 3,598,108 | 8/1971 | Jamshidi ........................ 606/21 |
| 3,630,192 | 12/1971 | Jamshidi ........................ 606/21 |
| 3,648,001 | 3/1972 | Anderson . |
| 3,938,527 | 2/1976 | Rioux . |
| 4,016,881 | 4/1977 | Rioux . |
| 4,733,671 | 3/1988 | Mehl . |
| 4,776,334 | 10/1988 | Prionas . |
| 4,781,198 | 11/1988 | Kanabrocki ........................ 128/654 |
| 4,917,100 | 4/1990 | Nottke . |
| 5,295,990 | 3/1994 | Levin . |

FOREIGN PATENT DOCUMENTS

WO93/04630  3/1993  WIPO .

Primary Examiner—Angela D. Sykes
Assistant Examiner—Sonya Harris-Ogugua
Attorney, Agent, or Firm—Caesar, Rivise, Bernstein, Cohen & Pokotilow, Ltd.

[57] ABSTRACT

A biopsy needle cauterizes the wound caused by the taking of a tissue specimen and the tissues in contact with the biopsy needle prior to withdrawal of the biopsy needle from a person, thereby minimizing bleeding and preventing the proliferation of any existing cancer cells along the path of insertion and withdrawal of the biopsy needle from the body. In contrast with existing biopsy needles, the tissue is excised by retraction of the stylet into the cannula, with the cutting edge being at the junction of the upper surface of the stylet and the front wall of the recess which holds the tissue specimen, rather than excising the tissue by sliding the cannula forward over the recess in the stylet with the cutting means at the leading edge of the cannula.

13 Claims, 2 Drawing Sheets

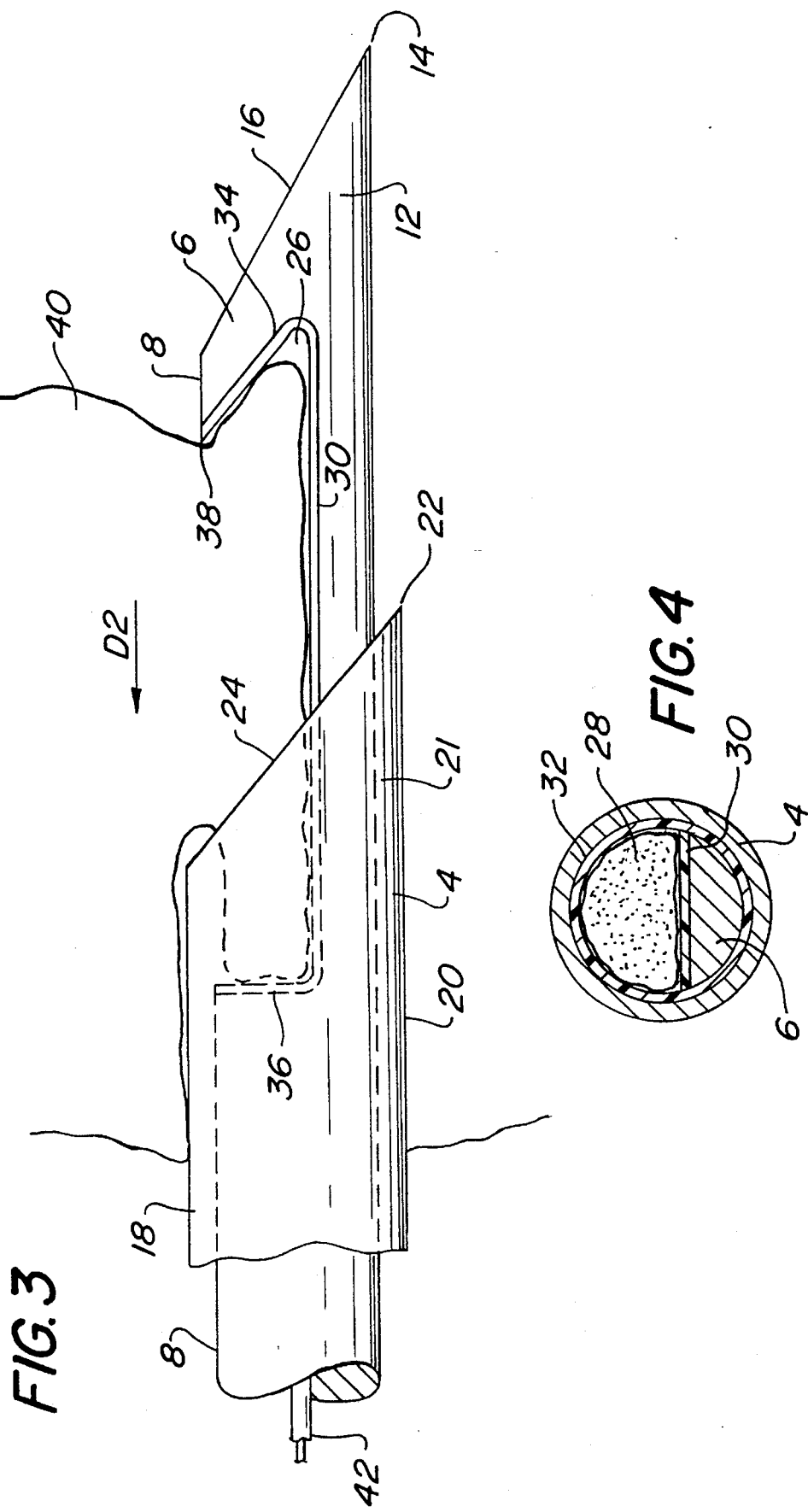

BIOPSY NEEDLE WITH CAUTERIZATION FEATURE

BACKGROUND OF THE INVENTION

This invention relates generally to biopsy needles, and more particularly to a biopsy needle with an improved capability for excising tissue specimens and for cauterizing the wound and the tissue in contact with the needle after the tissue specimen has been taken.

Various types of biopsy devices are known. Patents which disclose manual, spring operated biopsy devices include: U.S. Pat. No. 4,917,100 (Nottke) and U.S. Pat. No. 4,733,671 (Mehl). These biopsy devices comprise a cannula which is a hollow, rod-shaped member, and a stylet which is slidably mounted in the cannula. With the stylet positioned so that its end tip is adjacent the end of the cannula, the biopsy needle is inserted into the tissue of a person. The stylet has a notch or recess for holding the tissue specimen near its end, adjacent to the piercing tip. To take the tissue specimen, the stylet is then thrust forward into the area in which the specimen is desired. The cannula which has a sharp edge at its end, is then moved forward toward the end of the stylet, causing the sharp end of the cannula to excise tissue which is then held in the recess of the stylet. The biopsy device, with the specimen enclosed in the recess, is then removed from the body of the patient.

Devices which apply cauterizing heat to the body are shown in U.S. Pat. No. 4,016,881 (Rioux et al.) and U.S. Pat. No. 3,938,527 (Rioux et al.) which discloses a gun-shaped device which inserts electrodes into the body for cauterizing of tubes; and U.S. Pat. No. 4,776,334 (Prionas) which discloses a device for cauterizing tumors.

Other patents including U.S. Pat. No. 1,813,902 (Bovie); U.S. Pat. No. 3,648,001 (Anderson et al.); and U.S. Pat. No. 2,275,167 (Bierman) disclose surgical instruments which use electrical energy for cauterization or for cutting purposes.

My patent, U.S. Pat. No. 5,295,990, discloses a tissue sampling and removal device which comprises a pair of cutting jaws with a heat insulated inner surface defining a chamber for retaining the tissue cut by the jaws. A conductor carries electrical energy which heats the device, thereby cauterizing the tissues surrounding the jaws prior to removal of the excised tissue specimen.

Existing biopsy devices have several major shortcomings. The cutting of the tissue to excise a tissue specimen by moving the sharp end of the cannula forward over and past the recess in the stylet causes bunching of tissue and cutting which is often ragged and not sharp. Furthermore, if the biopsy needle is used to excise tissue specimens from a suspected cancer tumor or cancer infected area of the body, withdrawal of the needle after the specimen has been taken could well leave a trail of displaced cancer cells in the path of the removal of the biopsy needle, thereby proliferating the locations of the cancer.

In view of the foregoing, a biopsy needle with an improved cutting capability and which prevents the spread of cancer cells during the taking of tissue specimens as provided by the instant invention is needed.

OBJECTS OF THE INVENTION

Accordingly, it is the general object of the instant invention to provide a biopsy needle which improves upon, and which overcomes the shortcomings of, existing biopsy needles.

It is a further object of the instant invention to provide a biopsy needle which has improved cutting capability as compared to existing biopsy needles.

It is yet a further object of the instant invention to provide a biopsy needle which cauterizes the wound caused by the insertion and removal of the needle to minimize bleeding.

It is still yet a further object of the instant invention to provide a biopsy needle which cauterizes the tissue in contact with the needle after the taking of tissue specimens to prevent the spread of any existing cancer cells in the region of the location at which the specimen has been taken and along the path of removal of the biopsy needle.

It is another object of the instant invention to provide a biopsy needle which uses electrical current to heat the biopsy needle for cauterization of the wound and the tissues in contact with the biopsy needle after the taking of tissue specimens.

SUMMARY OF THE INVENTION

These and other objects of the instant invention are achieved by providing a biopsy needle which comprises a cannula, a stylet slidingly held in the cannula, means for inserting the needle into a person, means for excising tissue from the person, and means for removing the needle from the person. Cauterization means are provided to cauterize the wound to minimize bleeding and to cauterize the tissue in contact with the biopsy needle to prevent the spread of any existing cancer cells surrounding the wound along the path of removal of the biopsy needle after the tissue specimen has been taken.

An improved cutting means is provided by incorporating a sharp edge at the junction between the top surface of the stylet and the front wall of the recess in the stylet which holds the tissue specimen. Instead of moving the cannula forward toward the piercing end of the stylet to excise the tissue specimen, as is done with conventional biopsy needles, the stylet with the sharp edge near the end of the stylet is moved back toward the cannula to excise the tissue specimen.

DESCRIPTION OF THE DRAWING

Other objects and many of the intended advantages of this invention will be readily appreciated when the same becomes better understood by reference to the following detailed description, when considered in connection with the accompanying drawing wherein:

FIG. 3 is a side view of the biopsy needle showing the surrounding tissue with the stylet extended after the needle has been inserted in the body of a person; and FIG. 4 is a sectional view taken along the line 4—4 of FIG. 1 which shows the insulated chamber in which the tissue is held during catheterization prior to removal of the biopsy needle from the body of the person.

DETAILED DESCRIPTION OF THE PREFERRED EMBODIMENTS

Figure 1:
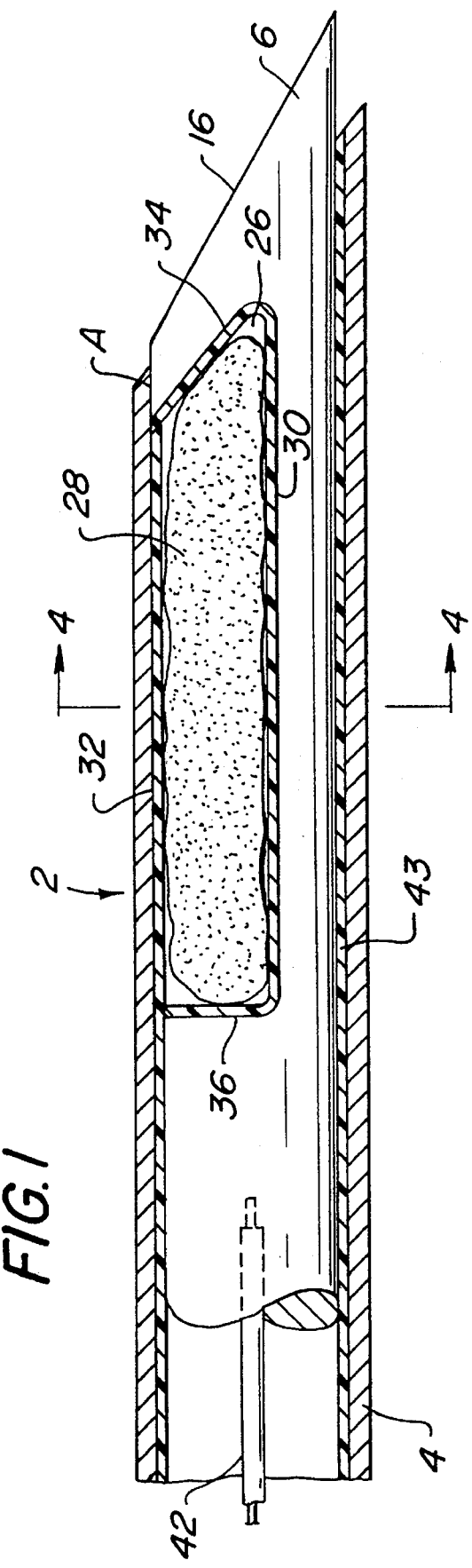
FIG. 1 is a sectional side view of the biopsy needle showing the stylet after it has been retracted into the cannula with the excised tissue specimen in the recess of the stylet.
Figure 2:
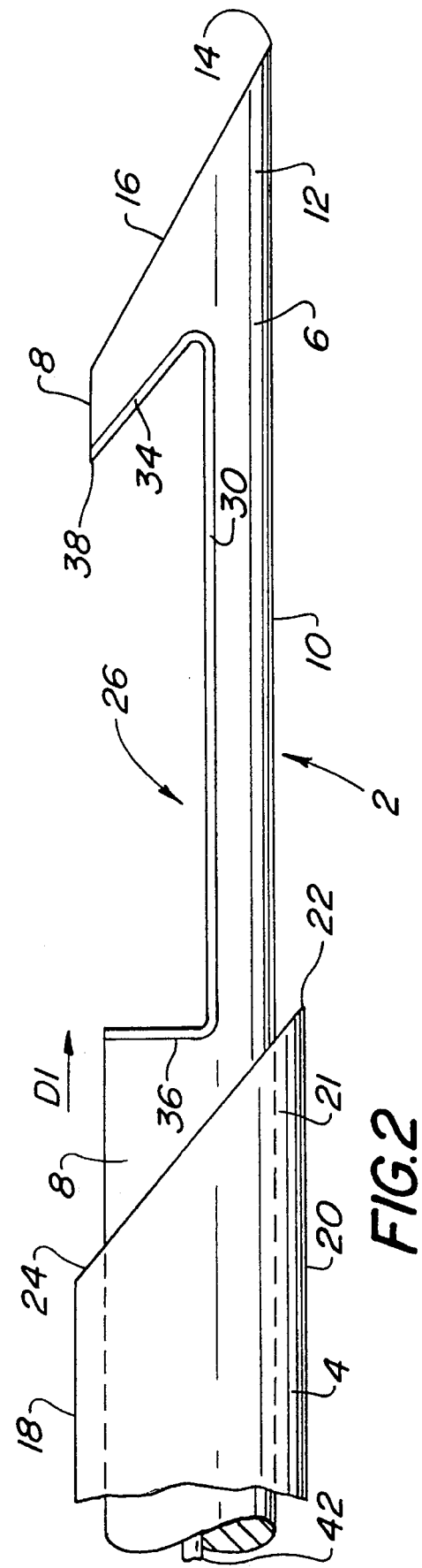
FIG. 2 is a side view of the biopsy needle with the stylet extended out from the cannula prior to retraction of the stylet back into the cannula for the taking of the tissue specimen.

Referring now in greater detail to the various figures of the drawing, wherein like reference characters refer to like parts, there is shown in FIGS. 1–3 the biopsy needle 2 of the instant invention. The biopsy needle 2 comprises a hollow, rod-shaped cannula 4 and a stylet 6, which is slidingly held in the cannula 4. The stylet 6 has an upper surface 8, a lower surface 10 and a proximal end 12. The proximal end 12 comprises a sloped end surface 16 which extends downwardly from the upper surface 8 to the lower surface 10. A piercing tip 14 is formed at the junction between the sloped end surface 16 and the lower surface 10, for insertion of the biopsy needle 2 into a person.

As can be seen in FIGS. 2 and 3, the cannula 4 has an upper surface 18, a lower surface 20, and a proximal end 21. The proximal end 21 comprises a sloped end surface 24 extending downwardly from the upper surface 18 to the lower surface 20 and a piercing tip 22 formed at the junction between the sloped end surface 24 and the lower surface 20.

The stylet 6 has a notch or specimen holding recess 26 extending downward from the upper surface 8. As can be seen in FIG. 1, the excised tissue specimen 28 is held in the specimen holding recess 26 after the specimen has been taken and the stylet 6 has been retracted back into the cannula 4.

The specimen holding recess 26 comprises an insulation bottom wall 30, a insulation front wall 34 and an insulation rear wall 36. Attached to the inner surface of the cannula 4 is an insulation circumferential wall 32. The walls 30, 32, 34 and 36 comprise insulating material which prevents the conduction of heat from outside the walls into the recess. Thus, when cauterization heat is applied to the biopsy needle, the excised tissue specimen 28 is protected from the heat. The walls 30, 32, 34 and 36 form a chamber (see FIGS. 1 and 4), which insulates the excised tissue specimen 28 from the cauterization heat which is applied to the biopsy needle 2 prior to removal of the biopsy needle from the patient, as will be explained later.

The procedure for the taking of the tissue specimen 28 and the cauterization of the wound and surrounding tissues will now be explained.

Initially, the stylet 6 is retracted fully into the cannula 4 so that the piercing tips 14 and 22 are adjacent. As can be seen in FIG. 2, the stylet 6 is then thrust forward in the direction $D_1$ of the arrow to extend the stylet 6 forward from the cannula 4 into the region of the person from which a tissue specimen 28 is desired. The arrow in FIG. 2 shows the forward direction $D_1$ of the stylet 6 when the stylet 6 is extended forward.

FIG. 3 shows the surrounding tissue 40 of the person, a part of which fills the specimen holding recess 26. As can be seen in the figure, the retraction of the stylet 6 back into the cannula 4 in the direction of the arrow $D_2$ excises the tissue specimen 28 from the body tissues of the person. The stylet 6 has a sharp cutting edge 38 formed at the junction between the insulated front wall 34 and the top surface 8 which cuts into the tissue 40 to excise the tissue specimen 28.

FIG. 1 shows the stylet fully retracted back into the cannula 4 with the excised tissue specimen 28 held in the specimen holding recess 26. As stated previously, an insulation chamber is formed by the insulation walls 30, 34 and 36 of the recess 26 and the insulation circumferential wall 32 to protect the excised tissue specimen 28.

The biopsy needle also includes a conductor 42 which applies electrical current to the biopsy needle 2 to heat the biopsy needle and thereby cauterize the wound caused by the excising of the tissue specimen and the tissue in contact with the biopsy needle 2 as it is removed from the body. The procedure is to re-thrust the biopsy needle 2 forward into the area from which the specimen was taken, then to apply cauterization heat before and while removing the biopsy needle 2 from the patient. This cauterization minimizes the bleeding of the wound caused by the insertion of the biopsy needle 2 and the excising of the tissue specimen 28. In addition, the cauterization kills existing cancer cells, preventing the proliferation of cancer cells, if they are present in the region in which the excised tissue specimen 28 has been taken, along the path of the removal of the biopsy needle from the body of the patient.

As can be further seen in FIG. 1, the inner surface of the cannula 4 has a ring of insulation 43. The small segment of the inner surface of the cannula 4 at A is not insulated. Therefore, the current can flow through the conductor 42 into the stylet 6 and then, at the area A, to the cannula 4 which acts as a return for the current.

A biopsy needle has been described which operates in a different manner than conventional biopsy needles and which provides a cleaner cutting technique than conventional biopsy needles. The biopsy needle 2 of the instant invention takes the excised tissue specimen 28 by retracting the stylet back into the cannula with a cutting edge at the junction between the top wall of the stylet and the front wall of the recess. By contrast, conventional biopsy needles take a tissue specimen by using a cutting edge at the front edge of the cannula and by thrusting the cannula forward to excise the tissue specimen 28 and to cover the recess 26 which holds the tissue specimen. Also, the biopsy needle of the instant invention automatically cauterizes the wound and the tissue in contact with the biopsy needle after the tissue specimen 28 has been taken and prior to removal of the biopsy needle from the patient, to minimize bleeding and to prevent the proliferation of cancer cells along the path of removal of the biopsy needle 2.

I claim:

1. A biopsy needle for obtaining tissue specimens from a person's tissues comprising: a cannula; a stylet having a sidewall slidingly held in said cannula; means for inserting said needle into said person; means for excising tissue specimens from said person and thereby forming a wound in the tissues, said excising means comprising a cutting edge in said sidewall; means for removing said needle from said person; and cauterization means for cauterizing the wound caused by said means for excising tissue and for cauterizing the tissues in contact with said biopsy needle wherein said cauterization means generates heat durng cauterization, said biopsy needle further comprising means for insulating said excised tissue specimen from the heat.

2. The biopsy needle of claim 1 wherein said stylet comprises a proximal end having an upper surface, a lower surface, and a sloping end surface extending from said upper surface to said lower surface thereby forming a junction where said sloping end surface intersects said lower end surface and wherein said means for inserting said biopsy needle comprises a piercing tip formed at the junction.

3. The biopsy needle of claim 2 wherein said stylet further comprises a tissue holding recess at said proximal end, and said recess comprises a front wall, a bottom wall and a rear wall.

4. The biopsy needle of claim 3 wherein said cutting edge is formed at the junction of said upper surface and said front wall.

5. The biopsy needle of claim 4 wherein said cauterization means comprises a conductor which carries electrical current.

6. The biopsy needle of claim 5 wherein said means for insulating said excised tissue from the heat caused by said cauterization means comprises insulating material in said front, rear and bottom walls and in a semi-circular upper wall formed in said cannula, said front, rear, bottom and upper walls forming an insulated chamber when said recess is located within said cannula.

7. The biopsy needle of claim 1 wherein said cauterization means comprises a conductor carrying electrical current.

8. The biopsy needle of claim 7 wherein said stylet further comprises a tissue specimen holding recess at said proximal end, said recess comprising a front wall, a bottom wall and a rear wall.

9. The biopsy needle of claim 8 wherein said means for insulating said excised tissue specimen from the heat caused by said cauterization means comprises insulating material in said front, rear and bottom walls and a semi-circular upper wall formed in said cannula, said front, rear, bottom and upper walls forming an insulated chamber when said recess is located within said cannula.

10. The biopsy needle of claim 9 wherein said stylet comprises a proximal end having an upper surface, a lower surface, a sloping end surface extending from said upper surface to said lower surface and wherein said means for inserting said biopsy needle comprises a piercing tip formed at the junction of said sloping end surface and said lower surface.

11. The biopsy needle of claim 10 wherein said stylet further comprises a tissue specimen holding recess at said proximal end, said recess comprising a front wall, a bottom wall and a rear wall.

12. A biopsy needle for obtaining tissue specimens from a person's tissues comprising a cannula, a stylet slidingly held in said cannula, said stylet comprising a sidewall having a cutting edge for excising said tissue specimens from said person and forming a wound in the tissues caused by said cutting edge, further comprising cauterization means for cauterizing the wound and for cauterizing the tissues in contact with said biopsy needle, wherein said cauterization means generates heat durng cauterization, said biopsy needle further comprising means for insulating said excised tissue specimen from the heat.

13. The biopsy needle of claim 12 wherein said cauterization means comprises a conductor carrying electrical current.

* * * * *